United States Patent [19]

Nagatani et al.

[11] Patent Number: 5,578,311
[45] Date of Patent: Nov. 26, 1996

[54] COSMETIC

[75] Inventors: Noboru Nagatani, Chiba; Makoto Torizuka, Tokyo; Takashi Komori, Chiba, all of Japan

[73] Assignee: Kao Corporation, Tokyo, Japan

[21] Appl. No.: 300,075

[22] Filed: Sep. 2, 1994

Related U.S. Application Data

[63] Continuation of Ser. No. 131,574, Oct. 4, 1993, abandoned, which is a continuation of Ser. No. 10,450, Jan. 25, 1993, abandoned, which is a continuation of Ser. No. 739,372, Aug. 2, 1991, abandoned.

[30] Foreign Application Priority Data

| Aug. 3, 1990 | [JP] | Japan | 2-205136 |
| Nov. 21, 1990 | [JP] | Japan | 2-316888 |
| Dec. 26, 1990 | [JP] | Japan | 2-414563 |

[51] Int. Cl.$^6$ .................................................. A61K 7/48
[52] U.S. Cl. ......................... 424/401; 424/59; 424/63; 424/69; 424/70.1; 424/70.12; 514/844; 514/845; 514/846; 514/937
[58] Field of Search ............................ 424/59, 63, 69, 424/401, 70.1, 70.12; 514/844, 845, 846, 937

[56] References Cited

U.S. PATENT DOCUMENTS

| 3,632,744 | 1/1972 | Paulsen | 424/69 |
| 3,975,352 | 8/1976 | Yoerger et al. | 524/462 |
| 4,801,445 | 1/1989 | Fukui et al. | 424/69 |
| 4,803,067 | 2/1989 | Brunetta et al. | 424/63 |
| 4,857,304 | 8/1989 | Ishiwatari et al. | 424/63 |

FOREIGN PATENT DOCUMENTS 0422984  4/1991  European Pat. Off. .

OTHER PUBLICATIONS

Patent Abstracts of Japan, vol. 12, No. 128, Apr. 20, 1988.

Primary Examiner—Jyothsan Venkat
Attorney, Agent, or Firm—Sughrue, Mion, Zinn, Macpeak & Seas

[57] ABSTRACT

Cosmetics comprising a hydrophobic powder or a fluorine compound-treated powder, and a liquid perfluoro organic compound are disclosed. These cosmetics are excellent in water repellency, water resistance, sebum resistance and oil resistance, prevents cosmetic components from the removal due to sweat or sebum, shows a good spreadability on the skin and gives a desirable feel at the use, for example, a moist and refreshing feel.

12 Claims, No Drawings

COSMETIC

This is a Continuation of application Ser. No. 08/131,574 filed Oct. 4, 1993, in turn a Continuation of application Ser. No. 08/010,450 filed Jan. 25, 1993, in turn a Continuation of application Ser. No. 07/739,372 filed Aug. 2, 1991, all abandoned.

FIELD OF THE INVENTION

This invention relates to a cosmetic. More particularly, it relates to a cosmetic which is excellent in water repellency and water resistance, further has an oil resistance, prevents cosmetic components such as pigments from the removal due to sweat or sebum and thus gives long-lasting makeup effect.

BACKGROUND OF THE INVENTION

Many water and oil repellent powders obtained by treating powders with a fluorine compound have been known as disclosed, for example, in JP-A-55-167209 (the term "JP-A" as used herein means an "unexamined published Japanese Patent Application"), JP-A-62-250074, JP-A-1-180811 and U.S. Pat. No. 3,632,744.

On the other hand, there has been required cosmetics, in particular, makeup cosmetics, which are excellent in, for example, water repellency and long-lasting makeup effect. When it is attempted to blend an oil commonly employed in these cosmetic products with a powder surface-treated with a fluorine compound in order to improve water repellency, however, the powder cannot be uniformly dispersed in the oil and thus any cosmetic having a good water repellency can be hardly obtained.

Accordingly, there has been required to develop a cosmetic, wherein a powder is uniformly dispersed, having a good water repellency, a good water resistance and a good long-lasting makeup effect.

On the other hand, powders have been added to cosmetics in order to color the skin or hair, to cover spots and freckles and to protect the skin from, for example, UV rays. In particular, an emulsified cosmetic, which shows a good feel and multi-functions, is blended with a powder to thereby give various cosmetic products including emulsified foundations, UV-protective emulsions and creams.

Recently, hydrophobic powders and hydrophobic-treated powders have been used in order to improve the adhesiveness to the skin and to impart water (sweat) resistance. When such a hydrophobic powder is to be stably blended with an emulsified cosmetic, however, it is required to thicken an oily phase used as a dispersion medium or to increase the amount of an emulsifier or a dispersant. Thus it is very difficult to obtain a product which shows a good feel and sustains powders in a stable state.

Further, in recent years, it has been attempted to use liquid perfluoro organic compounds in order to impart sebum and oil resistance to cosmetics, to make the skin or hair moist and smooth and to protect the skin and hair, as disclosed, for example, in JP-A-61-234928 and JP-A-63-107911. However, these perfluoro organic compounds are incompatible with other components commonly employed in cosmetics and thus it is difficult to obtain a stable emulsified cosmetic by using them.

Accordingly, there has been required to develop an emulsified cosmetic which has the desired characteristics of a liquid perfluoro organic compound and a hydrophobic powder, shows a good feel at the application and remains stable.

On the other hand, silicone oils, which have a smooth feel at the application compared with hydrocarbon oils and a good water repellency, have been frequently employed. In particular, a volatile silicone oil is used in cosmetics since it shows a good spreadability on the skin, a good adhesiveness due to the volatilization, and a high resistance against sweat. However, conventional cosmetics comprising a silicone oil is disadvantageous in that cosmetic components are easily removed by sebum and that they lack a moist feel at the application.

Accordingly, it is an object of the present invention to provide a cosmetic which is excellent in water repellency, water resistance, sebum resistance and oil resistance, prevents cosmetic components such as pigments and UV absorbers from the removal due to sweat or sebum, shows a good spreadability on the skin and gives a desirable feel at the application, for example, a moist and refreshing feel.

SUMMARY OF THE INVENTION

Under these circumstances, the present inventors have conducted extensive studies. As a result, they found that a cosmetic, in which a powder is uniformly dispersed in an oil, having a markedly improved-effect of preventing cosmetic components such as pigments from the removal due to sebum and an improved long-lasting makeup effect can be obtained by using a fluorine compound-treated powder in combination with a liquid perfluoro organic compound. Also, the present inventors further found that a surfactant, an aqueous medium, a perfluoro organic compound and a hydrophobic powder are compatible with each other and an emulsified cosmetic, which is excellent in a feel at the use and in stability, can be obtained by combining these components without deteriorating superior performances of the perfluoro organic compound and the hydrophobic powder. Thus the present invention has been completed.

Accordingly, the present invention provides, as the first embodiment of the invention, a cosmetic which comprises the following Components (A) and (B):

(A) a fluorine compound-treated powder; and (B) a liquid perfluoro organic compound;

wherein said fluorine compound-treated powder amounts from 5 to 95% by weight and said liquid perfluoro organic compound amounts from 5 to 95% by weight.

The present invention further provides, as the second embodiment of the invention, a cosmetic which comprises the following Components (A), (B) and (C):

(A) a fluorine compound-treated powder;

(B) a liquid perfluoro organic compound; and (C) a silicone oil.

The present invention furthermore provides, as the third embodiment of the invention, an emulsified cosmetic which comprises the following Components (A'), (B), (D) and (E):

(A') a hydrophobic powder;

(B) a liquid perfluoro organic compound;

(D) an aqueous medium; and (E) a surfactant.

DETAILED DESCRIPTION OF THE INVENTION

A cosmetic, which is the first embodiment of the present invention, comprising the following Components (A) and (B) will be described below in detail:

(A) a fluorine compound-treated powder; and (B) a liquid perfluoro organic compound,
wherein said fluorine compound-treated powder amounts from 5 to 95% by weight and said liquid perfluoro organic compound amounts from 5 to 95% by weight.

The fluorine compound-treated powder to be used as Component (A) in the first and second embodiments of the present invention is a powder treated with a fluorine compound. The fluorine compound-treated powder may be obtained by treating a powder with a fluorine compound, for example, a polyfluoroalkylphosphate are disclosed, for example, in U.S. Pat. No. 3,632,744, which is represented by the following general formula (I):

$$[C_sF_{2s+1}C_tH_{2t}O]_lPO(OM)_{3-l} \quad (I)$$

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group such as protonated mono-, di- or tri-ethanol amine; provided that the total of s and t is at least 8;
a resin having a fluoroalkyl group as disclosed, for example, in JP-A-55-167209; a ethylene tetrafluoride resin; a perfluoroalcohol; a perfluoroepoxy compound; a sulfoamide fluorophosphoric acid or a salt thereof; a perfluorosulfuric acid or a salt thereof; a perfluorocarboxylic acid or a salt thereof; and a perfluoroalkylsilane as disclosed, for example, in JP-A-2-218603 (e.g., silane coupling agents available from Shin-Etsu Silicone Co., Ltd. under the tradenames of LP-1T, LP-4T and LP-8T). Examples of the salt as mentioned above include an alkali metal salt, an alkaline earth metal salt, an ammonium salt, an alkanolamine salt, and the like.

JP-A-2-218603 states as follows:
2. Scope of Claim:
A cosmetic which is characterized by containing a hydrophibic powder obtained by treating one or two or more powders selected from inorganic powders and organic powders with a perfluoproalkylsilane represented by formula:

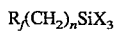
$$R_f(CH_2)_nSiX_3$$

(wherein $R_f$ represents a perfluoroakyl group having 1 to 12 carbon atoms; X's may be the same or different from each other and each represent an alkoxy group, a halogen atom or an alkyl group, provided that all X's are not alkyl groups at the same time; and n represents an integer of 1 to 5).

Among these fluorine compounds, the polyfluoroalkylphosphate of the general formula (I) is preferred for the fluorine compound-treated powder to be used as Component (A) in the first and second embodiments of the invention.

The material of the powder to be treated with the fluorine compound is not particularly restricted so long as it is substantially insoluble in water and oils (for example, pigments, UV absorbers ).

The form Of the powder to be treated is not particularly restricted. For example, those of plate form, amorphous form, scale form, spherical form or the like, or those having or not having pores can be used in the present invention. However, the powder of plate form or spherical form is preferred.

Also, the primary particle size of the powder to be treated is not particularly restricted so long as the powder is in the form of a powder. However, in the first and second embodiments of the invention, a powder having a primary particle size of from 0.01 to 80 μm is preferred and of from 0.1 to 20 μm is more preferred in view of the feel at the use.

Examples of the powder include inorganic pigments such as titanium oxide, iron oxide, ultramarine blue, zinc white, magnesium oxide, zirconium oxide, mica, sericite, talc, silica, kaolin, chromium hydroxide and carbon black; organic powders such as nylon powder, polymethyl methacrylate, styrene/divinylbenzene copolymer and polyethylene powder; and UV absorbers such as ultra-fine titanium dioxide powders, ultra-fine zinc oxide powders and fine zinc oxide flakes.

The method for treating the powder with the fluorine compound is not particularly restricted. For example, the fluorine compound is dissolved in an organic solvent (for example, benzene, toluene, acetone) with heating and then the powder is added thereto followed by stirring. After distilling off the solvent, the powder is coated with the fluorine compound. After the completion of the coating, the powder may be baked at a temperature higher than the melting point of the fluorine compound so as to achieve well drape. Prior to the coating with the use of an organic solvent, the powder may be dried by baking at 110° C. under reduced pressure for about 30 minutes to 80 hours. Thus the water repellency after the coating can be further improved. In these coating procedures, a mixture of two or more powders may be used. Furthermore, the powder may be simultaneously treated with known coating agent(s) other than the fluorine compound (for example, silicon, higher fatty acids, higher alcohols, esters, waxes), so long as the effects of the present invention are not deteriorated thereby.

The amount of the fluorine compound may vary depending on the kind of the compound. It is preferable to use the fluorine compound in an amount of from 0.1 to 50% by weight, more preferably from 2 to 20% by weight, based on the powder(s). When the amount of the fluorine compound is excessively small, a sufficient water repellency may not be obtained. When the amount of the fluorine compound is excessively large, on the other hand, the inherent good spreadability of the extender tends to be deteriorated.

These fluorine compound-treated powders can be used either alone or a mixture of two or more of them in the present invention. The fluorine compound-treated powders may be used in the first embodiment of the present invention in an amount of from 5 to 95% by weight, preferably from 5 to 70% by weight, based on the total weight of the composition.

The liquid perfluoro organic compound to be used as Component (B) in the present invention is a perfluoro organic compound which is in the form of a liquid at room temperature. Examples thereof include perfluorodecalin, perfluroadamantane, perfluorobutyltetrahydrofuran, perfluorooctane, perfluorononane, perfluoropentane, perfluorodecane, perfluorododecane and a perfluoro polyether represented by the following general formula (II):

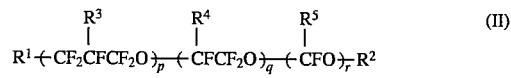
$$R^1 \text{-}(CF_2CFCF_2O)_p\text{-}(CFCF_2O)_q\text{-}(CFO)_r\text{-}R^2 \quad (II)$$
$$\phantom{R^1 \text{-}(CF_2C}|\phantom{F_2O)_p\text{-}(C}|\phantom{CF_2O)_q\text{-}(C}|$$
$$\phantom{R^1 \text{-}(CF_2C}R^3\phantom{F_2O)_p\text{-}(}R^4\phantom{F_2O)_q\text{-}(}R^5$$

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above value; provided that the molecular weight of the compound of the general formula (II) is from 500 to 100,000 and that all of p, q and r do not represent 0 at the same time.

It is not always necessary that these perfluoro groups given in parentheses in the general formula (II) align in that order. Further, either random polymerization or block polymerization maybe employed. Among these perfluoro polyethers, liquid ones having a viscosity of from 5 to 5,000 cs are preferable. More useful examples thereof include the compounds represented by the following general formula (III):

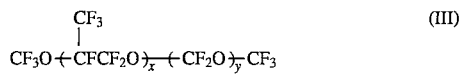

wherein x and y represent each such a number as to gave a molecular weight of from 500 to 10,000, provided that x/y is from 0.2 to 2, which are available from Montefluos Co., Ltd. under the tradenames of FOMBLIN MC-04 (average molecular weight: 1.500), FOMBLIN HC-25 (average molecular weights 3,200) and FOMBLIN HC-R (average molecular weights 6,600); and the compounds represented by the following general formula (IV):

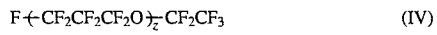

wherein z represents a number of from 4 to 500, which are available from Daikin Industries, Ltd. under the tradenames of Demnum S-20 (molecular weight (Mw): 25,000), Denmum S-65 (molecular Weight (Mw): 4,500), Demnum S-100 (molecular weight (Mw): 5,600) and Demnum S-200 (molecular weight (Mw): 8,400 ).

These liquid perfluoro organic compounds can be used either alone or a combination of two or more of them.

The liquid perfluoro organic compound(s) may be used in the first embodiment of the present invention in an amount of from 5 to 95% by weight, preferably from 5 to 60% by weight, based on the total weight of the composition.

In addition to the aforesaid essential Components (A) and (B), the cosmetic of the first embodiment of the present invention may further contain other components commonly employed in cosmetics, so long as the effects of the present invention are not deteriorated thereby. Examples of such components include solid/semisolid oils such as vaseline, lanolin, ceresin, microcrystalline wax, carnauba wax, candelilla wax, higher fatty acids and higher alcohols; liquid oils such as olive oil, jojoba oil, castor oil, squalane, liquid paraffin, ester oil, diglycerides, triglycerides and silicone oil; water-soluble and oil-soluble polymers; colorants such as inorganic and organic pigments, metal soap-treated or silicone-treated inorganic and organic pigments and organic dyes; surfactants such as anionic surfactants, cationic surfactants, nonionic surfactants and dimethylpolysiloxane/polyoxyalkylene copolymer; water preservatives; pigments; thickeners; pH controllers perfumes; UV absorbers; humectants; blood flow enhancing agents; agents causing cold sensation; antiperspirants; bactericides; and skin activators.

The cosmetic of this embodiment may be formulated into makeup cosmetics (for example, liquid foundation, powder foundation, rouge, eye shadow), medical cosmetics (for example, sunscreen) and medicines for external use (for example, antiinflamatry agent, skin protector) in a conventional manner.

The cosmetic of this embodiment, in which a fluorine compound-treated powder is uniformly dispersed, is excellent in water repellency and water resistance, has a good oil resistance, can prevent cosmetic components such as pigments from the removal due to sweat or sebum and shows an improved long-lasting makeup effect.

Now, a cosmetic, which is the second embodiment of the present invention, comprising the following Components (A), (B) and (C) will be described in detail:

(A) a fluorine compound-treated powder;

(B) a liquid perfluoro organic compound; and (C) a silicone oil.

As the silicone oil to be used as Component (C) in this embodiment, any silicone oil commonly used in cosmetics may be used. It is particularly preferable to use a volatile low molecular silicone oil or a cyclic silicone oil, from the viewpoint of the feel at the application. Examples of such silicone oils include low molecular silicone oils such as a methylpolysiloxane, a dimethylpolystloxane and a methylphenylpolysiloxane, whose viscosity are from 0.65 to 10 cs, and cyclic silicone oils such as a decamethylcycopentasiloxane and an octamethylcyclotetrasiloxane.

Either one of these silicone oils or a combination of two or more of them may be used in the present invention. The content of these silicone oils in the second embodiment of the present invention may preferably range from 1 to 70% by weight, more preferably 5 to 50% by weight, based on the total weight of the composition. When the content thereof is smaller than 1% by weight, the feel at the application tends to be deteriorated. When it exceeds 70% by weight, on the other hand, the long-lasting makeup effect tends to be deteriorated.

As the fluorine compound-treated powder to be used as Component (A) in this embodiment, those described above as the fluorine compound-treated powders may be used.

As the powder to be treated with a fluorine compound in Component (A), it is preferable to use those having a primary particle size of from 0.1 to 80 μm, more preferably from 0.1 to 20 μm.

Either one of these fluorine compound-treated powders or a combination of two or more of them may be used. These fluorine compound-treated powders may be preferably used in the second embodiment of the present invention in an amount of from 0.01 to 95% by weight, more preferably from 0.1 to 85% by weight, based on the total weight of the composition. When the content thereof is smaller than 0.01% by weight, the effects of this embodiment tends to be deteriorated. When it exceeds 95% by weight, on the other hand, the feel at the application tends to be deteriorated.

As the liquid perfluoro organic compound to be used as Component (B) in this embodiment, those described above as the liquid perfluoro organic compounds may be used.

Either one of these liquid perfluoro organic compounds or a combination of two or more of them may be used in this embodiment. These liquid perfluoro organic compounds may be used in the second embodiment of the present invention in an amount of from 1 to 70% by weight, more preferably from 5 to 50% by weight, based on the total weight of the composition. When the content thereof is smaller than 1% by weight, the dispersibility of the fluorine compound-treated powder in the cosmetic of this embodiment tends to be deteriorated. When it exceeds 70% by weight, on the other hand, the feel at the application of the cosmetic of this embodiment tends to be deteriorated.

In addition to the aforesaid essential Components (A), (B) and (C), the cosmetic of this embodiment may further contain, if required, various components commonly used in cosmetics as cited above, so long as the effects of the present invention are not deteriorated thereby.

The cosmetic of this embodiment may be formulated into any form (for example, powder, emulsion), without restriction. From the viewpoint of the feel at the application and effects, however, it maybe preferably formulated into an emulsified cosmetic. In this case, it is recommended to add from 10 to 80% by weight, preferably from 20 to 50% by weight, of water and from 0.1 to 10% by weight, preferably from 0.5 to 5% by weight, of surfactant(s), each based on the total weight of the composition, in addition to the aforesaid essential components.

The cosmetic of the present invention may be produced in a conventional manner. It is applicable as makeup cosmetics (for example, liquid foundation, powder foundation, rouge, eye shadow) and medical cosmetics (for example, sunscreen).

The cosmetic of this embodiment of the present invention can prevent cosmetic components such as pigments and UV absorbers from the removal due to sweat and sebum, shows a good spreadability on the skin and gives a good texture such as an appropriate moist and refreshing feel.

Next, an emulsified cosmetic, which is the third embodiment of the present invention, comprising the following components (A'), (B), (D) and (E) will be described in detail.

(A') a hydrophobic powder;

(B) a liquid perfluoro organic compound;

(D) an aqueous medium; and (E) a surfactant.

Examples of the surfactant to be used as Component (E) in this embodiment of the present invention include nonionic surfactants such as a monoglyceride, a sorbitan fatty acid ester, a sucrose fatty acid ester, a polyglycerol fatty acid ester, an alkanolamide, an amine oxide, a polyoxyethylene alkyl ether, a polyethylene glycol fatty acid ester, a polyoxyethylene sorbitan fatty acid ester, a polyoxyethylene glycerol monofatty acid ester, a polyoxyethylene propylene glycol monofatty acid ester, a polyoxyethylene hardened castor oil, a polyoxyethylene fatty acid amide, a polyoxyethylene alkylamine and an alkyl saccharide, anionic surfactants such as an alkyl sulfate salt, an alkyl ether sulfate, a fatty acid soap, an ether carboxylic acid and a salt thereof, an alkanesulfonate, an α-olefinesulfonate, a sulfonate of a higher fatty acid esters, dialkylsuofosuccinates, monoalkylsulfosuccinate, a polyoxyethylene monoalkylsulfosuccinate, a sulfonate of a higher fatty acid amide, a higher fatty acid alkylolamide sulfate salt, an acylated amino acid salt and an amino acid salt of a β-branched monoalkylphosphoric acid; cationic surfactants such as an alkyltrimethylammonium salt, a dialkyldimethylammonium salt, an alkyldimethylbenzylammonium salt and an alkylpyridinium salt; and amphoteric surfactant, such as an imidazoline surfactant, an amido amino acid salt, an alkylbetaine surfactant and an alkylsulfobetaine surfactant.

Either one of these surfactants or a combination of two or more of them may be used in the cosmetic of the third embodiment of the present invention. These surfactants may be preferably used in the cosmetic of the this embodiment in an amount of from 0.01 to 20% by weight, more preferably from 0 01 to 5% by weight based on the total weight of the composition. When the surfactant content is smaller than 0.01% by weight, the emulsion of this embodiment tends to be unstable. When this content exceeds 20% by weight, on the other hand, the hydrophobic properties of the powder tends be undesirably affected.

As the aqueous medium to be used as Component (D) in this embodiment, water may be used optionally together with water-soluble alcohol such as ethanol, glycerol, propylene glycol, dipropylene glycol or 1,3-butandiol. This aqueous medium is employed in order to dilute the surfactant of component (E). The content of the aqueous medium in this embodiment is not particularly restricted, it may preferably range from 0.5 to 40% by weight, more preferably from 2 to 30% by weight, based on total weight of the composition. When the content of the aqueous medium is smaller than 0.5% by weight the feel of the cosmetic of this embodiment tends to be deteriorated. When this content exceeds 40% by weight, on the other hand, the emulsion of this embodiment tends to be unstable.

As the liquid perfluoro organic compound to be used as Component (B) in this embodiment, the aforesaid liquid perfluoro organic compounds may be used.

The content of the liquid perfluoro organic compound in this embodiment is preferably from 40 to 98% by weight, more preferably from 50 to 90% by weight, based on the total weight of the composition. When the content is less than 40% by weight, the resulting composition tends to be difficult to be emulsified. When the content exceeds 98% by weight, on the other hand, the emulsion of this embodiment tends to be unstable.

The hydrophobic powder to be used as Component (A') in this embodiment includes common hydrophobic powders as well as hydrophobically treated powders prepared by hydrophobically treating the surface of one or two powders selected from among inorganic and organic powders.

The surface treatment maybe performed by, for example, an oil treatment method which comprises allowing the surface of a powder to adsorb a fat or making a powder lipophilic through esterification or etherification by using a functional group such as hydroxyl group; a metal soap treatment method by using a zinc or magnesium salt of a fatty acid; a silicone treatment method by using dimethylpolysiloxane or methylhydrogenpolysiloxane; and a method comprising treating with a fluorine compound having a perfluoroalkyl group. The "fluorine compound" to be used in this embodiment includes, for example, a polyfluoroalkylphosphate as disclosed, for example, in U.S. Pat. No. 3,632,744, which is represented by the following general formula (I):

$$[C_sF_{2s+1}C_tH_{2t}O]_lPO(OM)_{3-l} \qquad (I)$$

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group such as protonated mono-, di- or tri-ethanol amine; provided that the total of s and t is at least 8;
a resin having perfluoroalkyl groups as disclosed, for example, in JP-A-55-167209; an ethylene tetrafluoride resin; a perfluoroalcohol; a perfluoroepoxy compound; a sulfoamide fluorophosphoric acid or a salt thereof, a perfluorosulfuric acid or a salt thereof; a perfluorocarboxylic acid or a salt thereof; and perfluoroalkylsilane as disclosed, for example, in JP-A-2-218603; though the present invention is not restricted by these examples. Examples of the salt as mentioned above include an alkali metal salt, an alkaline earth metal salt, an ammonium salt, an alkanolamine salt, and the like.

Among these compound to be used for treating powders the polyfluoroalkylphosphate of the general formula (I) is preferred for the hydrophobic powder to be used as Component (A') in this embodiment.

The mother powder to be treated with these compounds is not particularly restricted so long as it is substantially insoluble in water and oils. Examples of the powder to be treated include inorganic pigments such as titanium oxide, iron oxide, ultramarine blue, zinc white, magnesium oxide, zirconium oxide, mica, sericite, talc, silica, kaolin, chromium hydroxide and carbon black; organic powders such as nylon powder, polymethyl methacrylate, styrene/divinylbenzene copolymer and polyethylene powder; and organic pigments. Among these powders, it is preferred to use those having a primary particle size of from 0.01 to 80 μm, more preferably from 0.1 to 20 μm.

Either one of these hydrophobic powders or a combination of two or more of them maybe used in the cosmetic of the third embodiment of the present invention as Component (A'). In this embodiment, these hydrophobic powders may be preferably used in an amount of from 0.01 to 50% by weight, more preferably from 0.1 to 30% by weight, based on the total weight of the composition. When the content of the hydrophobic powder is smaller than 0.01% by weight, the effects of this embodiment tends to be inferior. When it exceeds 50% by weight, on the other hand, the emulsion of this embodiment tends to be unstable.

In the emulsified cosmetic of this embodiment, a liquid oil can be added in addition to the liquid perfluoro organic compound (Component (B)). Examples of the liquid oil include olive oil, jojoba oil, castor oil, squalane, liquid paraffins, ester oils, diglycerides, triglycerides and silicone oils.

In this embodiment, the total content of Component (A'), Component (B) and liquid oil(s) other than Component (B) may be preferably 60% by weight or above, more preferably 70% by weight or above, based on the total weight of the composition. When this content is smaller than 60% by weight, the emulsified cosmetic of this embodiment tends to be unstable.

In addition to the aforesaid essential Components (A'), (B), (D) and (E), the cosmetic of this embodiment may further contain various components commonly used in cosmetics, as those cited above, so long as the effects of this embodiment of the present invention are not deteriorated thereby.

In the emulsified cosmetic of this embodiment, a large amount of the liquid perfluoro organic compound and a large amount of the hydrophobic powder can be stably blended. Such a stable emulsified cosmetic may be obtained by, for example, uniformly dissolving Components (D) and (E), optionally together with an arbitrary aqueous component, in an aqueous medium and slowly adding Component (A') suspended in Component (B) optionally together with an arbitrary liquid oil to the above-mentioned aqueous phase under starring. The cosmetic of this embodiment thus obtained may be used as cosmetic bases (for example, skin-care cream, cleansing cream, UV-protective cream), makeup cosmetics (for example, foundation, mascara, eye shadow), hair-care products (for example, hair-care gel, shampoo, hair dye), medical cosmetics and medicines for external use.

The emulsified cosmetic of this embodiment, in which the liquid perfluoro organic compound and the hydrophobic powder are stably contained without deteriorating the performance thereof, is excellent in the feel at the application and stability.

To further illustrate the present invention, the following Examples will be given.

PRODUCTION EXAMPLE 1

150 g of a powder was introduced into a round bottom flask (or a kneader) and heated to 60° C. while mixing. Next, 13 g Of $(C_6F_{13}CH_2CH_2O)_2P(O)OH$, which had been dissolved in 1500 g of isopropyl ether and heated to 50° C., was added thereto followed by mixing at 60° C. for 4 hours. After distilling off the isopropyl ether at 50° to 60° C. under reduced pressure, the residue was dried. Thus 157 g of a fluorine compound-treated powder was obtained.

PRODUCTION EXAMPLE 2

17 g of $(C_8F_{17}CH_2CH_2O)_2P(O)OH$ and 1500 g of isopropyl alcohol were added to a round bottom flask (or a kneader) and dissolved by heating to 60° C. Then 150 g of a powder was added thereto followed by mixing at 60° C. for 4 hours. After distilling off the isopropyl ether at 50° to 60° C. under reduced pressure, the residue was dried. Thus 161 g of a fluorine compound-treated powder was obtained.

EXAMPLE 1

(Two-layered liquid foundation)

A two-layered liquid foundation of the composition as given in Table 1 was prepared and the long-lasting makeup effect, aggregation and stability of this product were evaluated. Table 2 shows the results.

(Production method)

The oily phase was molten at room temperature and the pigment was added thereto followed by dispersing with a disper. Then the aqueous phase was added to the oily phase under stirring and thus the mixture was emulsified to thereby give the aimed liquid foundation.

TABLE 1

| Component | Example 1 | Comparative Example 1-1 | Comparative Example 1-2 |
|---|---|---|---|
| (1) Octamethylcyclotetrasiiloxane | 15.0 | 15.0 | 15.0 |
| (2) Dimethylpolysiloxans (KP-96A, tradename, a product of Shin-Etsu Silicone Co., Ltd.; 6 cs) | — | — | 15.0 |
| (3) Perfluoro polyether (FOMBLIN MC-04, tradenamer a product of Montefluos Co., Ltd.) | 15.0 | 15.0 | — |
| (4) Dimethylpolysiloxane polyoxyalkylene copolymer (SH377fc, tradename, a product of Toray Silicone Co., Ltd.) | 1.0 | 1.0 | 1.0 |
| (5) Glycerol | 2.0 | 2.0 | 2.0 |
| (6) Ethanol | 10.0 | 10.0 | 10.0 |
| (7) Water | balance | balance | balance |
| (8) Fluorine compound-treated pigment (Production Example 2) | | | |
| Titanium oxide | 6.0 | — | 6.0 |
| Sericite | 8.0 | — | 8.0 |
| Iron oxide (red, black, yellow) | 1.5 | — | 1.5 |

TABLE 1-continued

| Component | Example 1 | Comparative Example 1-1 | Comparative Example 1-2 |
|---|---|---|---|
| (9) Silicone-treated pigment (marketed product treated with polymethylhydrogensiloxane) | | | |
| Titanium oxide | — | 6.0 | — |
| Sericite | — | 8.0 | — |
| Iron oxide (red, black, yellow) | — | 1.5 | — |
| (10) Perfume | appropriate amount | appropriate amount | appropriate amount |

Note: All values indicated in Table 1 above are % by weight based on the total weight of the composition.

(Evaluation method)
Long-lasting makeup effect:
The long-lasting makeup effect of a sample was organoleptically evaluated by 10 skilled panelists in accordance with the following criteria:
A: Evaluated as high by 8 or more panelists
B: Evaluated as high by 4 to 7 panelists
C: Evaluated as high by less than 4 panelists
Aggregation:
The aggregation in a liquid foundation was examined with the naked eye immediately after the production.
A: Not aggregated
B: Aggregated
Stability:
A liquid foundation was stored at 40° C. for a month and then evaluated in accordance with the following criteria.
A: Uniformly dispersed by shaking lightly
B: Never uniformly dispersed even by shaking vigorously

TABLE 2

| | Long-lasting make-up effect | Aggregation (immediately after production) | Stability (40° C., 1 month) |
|---|---|---|---|
| Example 1 | A | A | A |
| Comparative Example 1-1 | B | A | B |
| Comparative Example 1-2 | C | B | B |

As Table 2 clearly shows, the liquid foundation of the present invention was superior in long-lasting makeup effect and stability to those containing either fluorine-treated pigment or the fluorine oil alone.

EXAMPLE 2

(Powder foundation)

| Component | Content (% by weight) |
|---|---|
| (1) Fluorine compound-treated powder (Production Example 2) | |
| Titanium oxide | 10.0 |
| Sericite | 30.0 |
| Mica | balance |
| Kaolin | 5.0 |
| Red iron oxide | 2.5 |
| Yellow iron oxide | 2.0 |
| Black Iron oxide | 0.1 |
| (2) Polyethylene powder | 8.0 |
| (3) Squalane | 2.0 |
| (4) Perfluoro polyether (FOMBLIN HC-04, tradename, a product of Montefluos Co., Ltd.) | 10.0 |
| (5) Preservative | 0.1 |
| (6) Perfume | appropriate amount |

(Production method)
The pigment components were mixed together and ground in a mill. Then the ground mixture was transferred into a high-speed blender. The binder and other components were mixed uniformly and then added to the pigment. The obtained mixture was treated with a mill and dressed by sieving. After allowing to stand for several days, the mixture was compression molded in a container such as a metal dish to thereby give a powder foundation.

EXAMPLE 3

(Rouge)

The procedure of Example 2 was repeated to thereby give a rouge.
(Composition)

| Component | Content (% by weight) |
|---|---|
| (1) Fluorine compound-treated powder (Production Example 1) | |
| Kaolin | balance |
| Mica | 13.0 |
| Titanium oxide | 12.0 |
| Iron oxides (red, black, yellow) | 5.0 |
| (2) Organic pigment (Red No. 202) | 2.4 |
| (3) Squalane | 7.5 |
| (4) Perfluoro polyether (FOMBLIN HC-04, tradename, a product of Montefluos Co., Ltd.) | 15.0 |
| (5) Preservative | 0.1 |
| (6) Perfume | appropriate amount |

EXAMPLE 4

(Powder eye shadow)

(Composition)

| Component | Content (% by weight) |
|---|---|
| (1) Fluorine compound-treated powder (Production Example 1) | |
|     Mica titanium | 35.0 |
|     Sericite | 24.0 |
|     Mica | 10.0 |
|     Coloring pigment | 15.0 |
| (2) Zinc stearate | 5.0 |
| (3) Zinc laurate | 3.0 |
| (4) Perfluoro polyether (FOMBLIN HC-04, tradename, a product of Montefluos Co., Ltd.) | 8.0 |

(Production method)

The powder components other than mica titanium were mixed together and ground. Then the mica titanium was added thereto. Next, the procedure of Example 2 was repeated to thereby give the target powder eye shadow.

EXAMPLE 5

(Sunscreen emulsion (W/O type))

The procedure of Example 1 was repeated to thereby give a sunscreen emulsion.
(Composition)

| Component | Content (% by weight) |
|---|---|
| (1) Octamethylcyclotetragiloxane | 25.0 |
| (2) Perfluoro polyether (FOMBLIN HC-04, tradename, a product of Montefluos Co., Ltd.) | 10.0 |
| (3) Dimethylpolysiloxane/polyoxyalkylene copolymer (SH3775C, product of Toray Silicone Co., Ltd.) | 1.0 |
| (4) Glycerol | 2.0 |
| (5) Ethanol | 5.0 |
| (6) Water | balance |
| (7) Fluorine compound-treated zinc oxide (Production Example 1) | 7.5 |
| (8) Octyl methoxycinnaxote | 2.0 |
| (9) Perfume | appropriate amount |

Each of the cosmetics or Examples 2 to 5 was excellent in the long-lasting makeup effect and the stability.

EXAMPLE 6

Emulsified cosmetics of the compositions as given Table 3 were produced and the stabilities thereof were evaluated. Table 3 shows the results.
(production method)

The perfluoro phase specified below was slowly added to the aqueous phase specified below under stirring. After the completion of the addition, stirring was further continued for 30 minutes.

(Evaluation method)

After storing at 40° C. for 7 days, the stability of each product was evaluated based on the appearance.

TABLE 3

| Component (% by weight) | Product of the Invention 2-A | Product of the Invention 2-B | Product of the Invention 2-C | Comparative Product 2-A |
|---|---|---|---|---|
| aqueous phase*1 | 20 | 30 | 40 | 50 |
| oily phase*2 | 80 | 70 | 60 | 50 |
| Stability | very good | very good | good | separated |

Notes;
*1 10% by weight aqueous solution of polyoxyethylone (20) sorbitan monolaurate.
*2 1% by weight silicone-treated talc suspension of perfluoro polyether (FOMBLIN HC-04) solution.

EXAMPLE 7

(Foundation)

Emulsified cosmetics of the compositions as given in Table 4 were produced in the following production method and the applicability on the skin, the feel immediately after the application and the long-lasting makeup effect of each product were evaluated. Table 5 shows the results.

TABLE 4

| Component (% by weight) | Product of the Invention 2-D | Product of the Invention 2-B | Comparative Product 2-C |
|---|---|---|---|
| (1) Polyoxyethylene (40) hardened castor oil | 1.0 | 1.0 | 3.0 |
| (2) Polyoxyethylone (20) sorbitan isostearate | 1.0 | 1.0 | 3.0 |
| (3) Glycerol | 7.0 | 7.0 | 7.0 |
| (4) Water | 14.0 | 14.0 | 10.0 |
| (5) Perfluoro polyether (FOMBLIN HC-40) | 50.0 | 50.0 | 50.0 |
| (6) Dimethylpolysiloxane (6 cs) | 5.0 | 5.0 | 5.0 |
| (7) Octamethylcyclotetrasiloxane | 10.0 | 10.0 | 10.0 |
| (8) Fluorine compound-treated powder (Production Example 1) | | | |
|     Titanium oxide | 2.0 | 2.0 | 2.0 |
|     Iron oxide | 1.5 | 1.5 | 1.5 |
|     Sericite | 8.5 | 8.5 | 9.5 |

(Production method)

Product of the Invention 2-D and Comparative Product 2-C:

To an aqueous phase, in which the components (1) to (4) were uniformly dissolved, a uniform mixture of the components (6) and (7) was slowly added under stirring. Next, a perfluoro phase, in which the component (8) was suspended in the component (5), was similarly added thereto followed by stirring for 60 minutes.

Comparative Product 2-B:

An aqueous phase, in which the components (1) to (4) were uniformly dissolved, a perfluoro phase, in which the component (8) was suspended in the component (5), and a uniform mixture of the components (6) and (7) were mixed and stirred for 60 minutes.

(Results)

Comparative Product 2-B completely separated out and thus could not be evaluated. 10 Female panelists used the emulsified foundations, i.e., Product of the Invention 2-D and Comparative Product 2-C in practice and evaluated the 5 items given in Table 5 in accordance with the following criteria.

(Evaluation criteria)
1. Applicability:
   A: Highly spreadable and easily applied
   B: Somewhat highly spreadable and easily applied
   C: Somewhat less spreadable and hardly applied
   D: Less spreadable and hardly applied
2. Feel immediately after the application:
   A: Dry land good
   B: Somewhat dry
   C: Somewhat sticky
   D: Sticky and poor
3. Long-lasting makeup effect:
   A: No change in makeup
   B: Little change in makeup
   C: Some change in makeup
   D: Serious change in makeup

TABLE 5

| Evaluation Item | Product of the invention 2-D | Comparative Product 2-C |
| --- | --- | --- |
| Applicability | A | B |
| Peal immediately after the application | A | C |
| Long-lasting makeup effect | A | D |
| Sweat test* | no removal | uneven due to removal by sweat |

*Observed after 30 minutes in a room of 40° C., RH 75%.

EXAMPLE 8

(UV-protective skin care cream)

An UV-protective skin care cream of the following composition was produced in the following production method.

The obtained skin care cream showed a refreshing and good feel at the application and was excellent in appearance and stability.
(Production method)

To an aqueous phase, in which the components (1) to (5) were uniformly dissolved, an oily phase of the components (6) to (8) was slowly added under stirring. Then a perfluoro phase, in which the component (10) was suspended in the component (9), was similarly added thereto and the mixture was further stirred for 30 minutes.
(Composition)

| Component | Content (% by weight) |
| --- | --- |
| (1) Polyoxyethylone (50) hardened castor oil | 0.5 |
| (2) Polyoxyethylene (20) sorbitan palmitate | 1.0 |
| (3) 1,3-Butylene glycol | 5.0 |
| (4) Glycerol | 5.0 |
| (5) Water | 17.5 |

-continued

| Component | Content (% by weight) |
| --- | --- |
| (6) Squalane | 5.0 |
| (7) Jojoba oil | 5.0 |
| (8) Octamethyleyclotetrasiloxane | 20.0 |
| (9) Perfluoro polyether (FOMBLIN HC-04) | 40.0 |
| (10) Fluorine compound-treated titanium oxide (Production Example 2) | 1.0 |

EXAMPLE 9

(UV-protective hair care cream)

An UV-protective hair care cream of the following composition was produced in the following production method.

The obtained hair care cream showed a good feel at the application and a high stability. Further, the oil component contained therein made the hair glossy and exerted an extremely good brushing care effect.
(Production method)

To an aqueous phase, in which the components (1) to (3) were uniformly dissolved, a uniform mixture of the components (5) and (6) was slowly added under stirring. Next, a perfluoro phase, in which the component (7) was suspended in the component (4), was similarly added and the obtained mixture was further starred for 60 minutes.
(Composition)

| Component | Content (% by weight) |
| --- | --- |
| (1) Polyoxyethylene (25) octyldodecyl ether | 2.0 |
| (2) Propylene glycol | 1.0 |
| (3) Water | 10.0 |
| (4) Perfluoro polyether (FOMBLIN 2HC-04) | 80.0 |
| (5) Dimethylpolysiloxane (6 cs) | 5.0 |
| (6) Oxybenzone | 1.0 |
| (7) Fluorine compound-treated titanium oxide (Production Example 1) | 1.0 |

EXAMPLE 10

(Cosmetic base cream)

A cosmetic base cream of the following composition was produced in the following production method.

when the obtained, cosmetic base cream was used, the texture of the skin was improved and a powdery type foundation could be easily applied thereon. Further, this product showed an improved long-lasting makeup effect and had a high stability.
(Production method)

To an aqueous phase, in which the components (1) to (4) were uniformly dissolved, a uniform mixture of the components (6) and (7) was slowly added under stirring. Next, a perfluoro phase, in which the component (8) was suspended in the component (5), was similarly added and the obtained mixture was further stirred for 60 minutes.

(Composition)

| Component | Content (% by weight) |
| --- | --- |
| (1) Polyoxyethylons (20) sorbitan isostearate | 0.5 |
| (2) Polyoxyethylene (25) octyldodecyl ether | 1.0 |
| (3) Glycerol | 6.5 |
| (4) Water | 17.0 |
| (5) Perfluoro polyether (FOMBLIN HC-25) | 30.0 |
| (6) Olive oil | 2.0 |
| (7) Octamethylcyclotetrasiloxane | 38.0 |
| (8) Fluorine compound-treated talc (Production Example 2) | 3.0 |
| (9) Stearic acid-treated mica | 2.0 |

EXAMPLE 11

(Cleansing cream)

A cleansing cream of the following composition was produced in the following production method.

When the skin was rubbed down with the use of an appropriate amount of the obtained cleansing cream, oily and fluorine stains come to the surface of the skin. After washing away with running water, these stains and the cream could be completely removed in the form of a cloudy suspension. The oily and fluorine stains could come to the surface very rapidly and stains in skin depressions could be easily removed. After washing, a highly refreshing feel was obtained.

(Production method)

To an aqueous phase, in which the components (1) to (4) were uniformly dissolved, a uniform mixture of the components (6) to (8) was slowly added under stirring. Next, a perfluoro phase, in which the component (9) was suspended in the component (5), was similarly added and the obtained mixture was further stirred for 60 minutes.

(Composition)

| Component | Content (% by weight) |
| --- | --- |
| (1) Polyoxyethylene (25) octyldodecyl ether | 1.5 |
| (2) Polyoxyethylene (20) sorbitan monolaurate | 1.5 |
| (3) Propylene glycol | 14.5 |
| (4) Water | 10.0 |
| (5) Perfluoro polyether (FOMBLIN HC-04) | 30.0 |
| (6) Octamethylcyclotetrasiloxane | 30.0 |
| (7) Jojoba oil | 5.0 |

-continued

| Component | Content (% by weight) |
| --- | --- |
| (9) Squalane | 6.0 |
| (9) Fluorine compound-treated polymethyl methacrylate (Production Example 2) | 1.0 |
| (10) Methylhydrogensiloxane-treated mica | 0.5 |

EXAMPLE 12 AND COMPARATIVE EXAMPLES 3-1 TO 3-4

(Two-layered liquid foundation)

A two-layered liquid foundation of each composition as given in Table 6 was prepared in the following production method and the long-lasting makeup effect, aggregation, feel at the application and stability of each product were evaluated in the following evaluation method. Table 7 shows the results.

(Production method)

The oily phase was molten at room temperature and the pigment was added thereto followed by dispersing with a disper. Then the aqueous phase was added under stirring and thus the mixture was emulsified to thereby give the aimed liquid foundation.

(Evaluation method)

Long-lasting makeup effect:

The long-lasting makeup effect of a sample was organoleptically evaluated by 10 skilled panelists in accordance with the following criteria:

A: Evaluated as high by 8 or more panelists

B: Evaluated as high by 4 to 7 panelists

C: Evaluated as high by less than 4 panelists

Aggregation:

The aggregation in a liquid foundation was examined with the naked eye immediately after the production.

A: Not aggregated

B: Aggregated

Feel at the application:

The feel at the application of a liquid foundation was organoleptically evaluated by 10 skilled panelists based on the same criteria as those used in the evaluation of the long-lasting makeup effect.

Stability:

A liquid foundation was stored at 40° C. for a month and then evaluated in accordance with the following criteria.

A: Uniformly dispersed by shaking lightly

B: Never uniformly dispersed even by shaking vigorously

TABLE 6

| Component | Example 2 | Comparative Example 3-1 | Comparative Example 3-2 | Comparative Example 3-3 | Comparative Example 3-4 |
|---|---|---|---|---|---|
| (1) Fluorine compound-treated powder (the following pigments were treated in accordance with Production Example 2) | | | | | |
| Titanium oxide | 6.0 | 6.0 | 6.0 | — | — |
| Sericite | 8.0 | 8.0 | 8.0 | — | — |
| Iron oxide (red, black, yellow) | 1.2 | 1.2 | 1.2 | — | — |
| (2) Silicone-treated powder (polymethylhydrogensiloxane-treated pigments) | | | | | |
| Titanium oxide | — | — | — | 6.0 | 6.0 |
| Sericite | — | — | — | 8.0 | 8.0 |
| Iron oxide (red, black, yellow) | — | — | — | 1.2 | 1.2 |
| (3) Octamethylcyclctetrasiloxane | 20.0 | — | 20.0 | 20.0 | — |
| (4) Dimethylpolysiloxane (KF-96A, tradename, a product of Shin-Etsu Silicone Co., Ltd.; 6 cs) | 2.0 | — | 12.0 | 2.0 | — |
| (5) Dimethylpolysiloxane polyoxyalkylene copolymer | 1.0 | 1.0 | 1.0 | 1.0 | 1.0 |
| (6) Perfluoro polyether (FOMBLIN HC-04, tradename, a product of Montefluos) Co., Ltd.) | 10.0 | 32.0 | — | — | 32.0 |
| (7) Glycerol | 2.0 | 2.0 | 2.0 | 2.0 | 2.0 |
| (8) Ethanol | 15.0 | 15.0 | 15.0 | 15.0 | 15.0 |
| (9) Water | balance | balance | balance | balance | balance |
| (10) Perfume | appropriate amount | appropriate amount | appropriate amount | appropriate amount | appropriate amount |

Note: All values indicated in Table above are % by weight based on the total weight of the composition.

TABLE 7

| | Long-lasting makeup effect | Aggregation (immediately after production) | Feel at the application | Stability (40° C., 1 month) |
|---|---|---|---|---|
| Example 12 | A | A | A | A |
| Comparative Example 3-1 | A | B | C | B |
| Comparative Example 3-2 | B | B | C | B |
| Comparative Example 3-3 | C | A | B | A |
| Comparative Example 3-4 | C | A | C | B |

As Table 7 clearly shows, the liquid foundation of the present invention (Example 12) was superior in long-lasting makeup effect, feel at the application and stability to those containing either fluorine-treated pigment or the fluorine oil alone (Comparative Examples 3-1 to 3-4).

EXAMPLE 13

(Creamy foundation)

The procedure of Example 12 was repeated to thereby give a creamy foundation of the following composition.

(Composition)

| Component | Content (% by weight) |
|---|---|
| (1) Fluorine compound-treated powder (the following pigments were treated in accordance with Production Example 2) | |
| Titanium oxide | 6.0 |
| Semicite | 8.0 |
| Iron oxide (red, yellow, black) | 1.2 |
| (2) Decamethylcyclopentasiloxane | 15.0 |
| (3) Dimethylpolysiloxane (KF-96A, tradename, a product of Shin-Etsu Chemical Co., Ltd.; 6 cs) | 10.0 |
| (4) Dimethylpolysiloxane polyoxyalkylene copolymer | 1.0 |
| (5) Perfluoro polyether (FOMBLIN HC-04, tradename, a product of Montefluos Co., Ltd.) | 20.0 |
| (6) Glycerol | 2.0 |
| (7) Water | balance |
| (8) Perfume | appropriate amount |

EXAMPLE 14

(Powder foundation)

The powders given in the following composition were mixed together and ground with a mill. The ground mixture was when transferred into a high-speed blender and other components including the binder were uniformly mixed therewith. After uniformly mixing, the mixture was treated with a mill and dressed by sieving. Then it was allowed to stand for several days and compression-molded in a container such as a metal dash. Thus a powder foundation was obtained.

(Composition)

| Component | Content (% by weight) |
|---|---|
| (1) Fluorine compound-treated powder (the following pigments were treated in accordance with Production Example 2) | |
| Titanium oxide | 10.0 |
| Sericite | 30.0 |
| Talc | 30.0 |
| Kaolin | 5.0 |
| Red iron oxide | 2.0 |
| Yellow iron oxide | 2.5 |
| Black iron oxide | 0.1 |
| Polyethylene powder | 4.0 |
| (2) Squalane | 2.0 |
| (3) Dimethylpolysiloxane (KP-96A, tradename, a product of Shin-Etsu Chemical Co., Ltd.; 6 cs) | 7.0 |
| (4) Perfluoro polyether (FOMBLIN HC-25, tradename, a product of Montefluos Co., Ltd.) | 7.0 |
| (5) Preservative | appropriate amount |
| (6) Perfume | trace |

EXAMPLE 15

(Rouge)

The procedure of Example 14 was repeated to thereby give a rouge of the following composition.
(Composition)

| Component | Content (% by weight) |
|---|---|
| (1) Fluorine compound-treated powder (the following pigments were treated in accordance with Production Example 2) | |
| Kaolin | 50.0 |
| Mica | 13.0 |
| Titanium oxide | 12.0 |
| Iron oxide (red, yellow, black) | 5.0 |
| (2) Organic pigment (Red No. 202) | 2.4 |
| (3) Dimethylpolysiloxane (XF-96A, a product of Shin-Etsu Chemical Co., Ltd.; 6 cs) | 7.4 |
| (4) Perfluoro polyether (FOMBLIN HC-04, tradename, a product of Montefluos Co., Ltd.) | 10.0 |
| (5) Preservative | appropriate amount |
| (6) Perfume | trace |

EXAMPLE 16

(Powder eye shadow)

The procedure of Example 14 was repeated except that the pigments other than the mica titanium were preliminary mixed and ground followed by adding the mica titanium. Thus a powder eye shadow of the following composition was obtained.

(Composition)

| Component | Content (% by weight) |
|---|---|
| (1) Fluorine compound-treated powder following pigments were treated in accordance with Production Example 2) | |
| Mica titanium | 5.0 |
| Sericite | 36.0 |
| Mica | 24.0 |
| Iron oxide (red, yellow, black) | 2.0 |
| Ultramarine blue | 10.0 |
| Prussian blue | 6.0 |
| (2) Dimethylpolysiloxane (KF-96, tradename, a product of Shin-Etsu Chemical Co., Ltd.; 6 cs) | 6.0 |
| (3) Perfluoro polyether (FOMBLIN HC-04, tradename, a product of Montefluos Co., Ltd.) | 6.0 |
| (4) Squalane | 3.0 |
| (5) Sorbitan trioleate | 1.0 |
| (6) Preservative | appropriate amount |
| (7) Perfume | trace |

EXAMPLE 17

(Sunscreen emulsion)

The procedure of Example 12 was repeated to thereby give a sunscreen emulsion of the following composition.
(Composition)

| Component | Content (% by weight) |
|---|---|
| (1) Octamethylcyclotetrasiloxane | 25.0 |
| (2) Perfluoro polyether (FOMBLIN HC-04, tradename a product of Montefluos Co., Ltd.) | 10.0 |
| (3) Dimethylpolysiloxane polyoxyalkylene copolymer | 1.0 |
| (4) Glycerol | 2.0 |
| (5) Ethanol | 5.0 |
| (6) Water | balance |
| (7) Fluorine compound-treated zinc oxide (zinc oxide was treated in accordance with Production Example 1) | 7.5 |
| (8) Octyl methoxycinnamate | 2.0 |
| (9) Perfume | appropriate amount |

Each of the cosmetics of Examples 13 to 17 was excellent in the long-lasting makeup effect and feel at the application and the fluorine compound-treated powder was well dispersed therein.

The cosmetic of the present invention is excellent in water repellency, water resistance, sebum resistance and oil resistance. It prevents cosmetic components such as pigments and UV absorbers from the removal due to sweat or sebum. Further, it shows a good spreadability on the skin and gives an excellent feel, for example, an appropriate moist and refreshing feel.

While the invention has been described in detail and with reference to specific examples thereof, it will be apparent to one skilled in the art that various changes and modifications can be made therein without departing from the spirit and scope thereof.

What is claimed is:

1. A cosmetic comprising the following components (A) and (B):

(A) from 5 to 95% by weight of a fluorine compound-treated powder,
wherein said fluorine compound is selected from the group consisting of polyfluoroalkylphosphate represented by the following formula (I):

$$[C_sF_{2s+1}C_tH_{2t}O]_lPO(OM)_{3-l} \quad (I)$$

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8; perfluoroalcohol; perfluoroepoxy compound; sulfoamide fluorophosphoric acid or a salt thereof; perfluoro-sulfuric acid or a salt thereof; perfluorocarboxylic acid or a salt thereof; and perfluoroalkylsilane, and said powder is selected from the group consisting of titanium oxide, iron oxide, ultramarine blue, zinc white, magnesium oxide, zirconium oxide, mica, sericite, talc, silica, kaolin, chromium hydroxide, carbon black, nylon powder, polymethyl methacrylate powder, styrene/divinylbenzene copolymer powder, polyethylene powder, UV-absorbing ultrafine titanium dioxide powder, UV-absorbing ultrafine zinc oxide powder and UV-absorbing fine zinc oxide flakes; and (B) from 5 to 95% by weight of a liquid perfluoro organic compound selected from the group consisting of perfluorodecalin, perfluorobutyltetrahydrofuran, perfluorooctane, perfluorononane, perfluoropentane, perfluorodecane, perfluorododecane and perfluoro polyether represented by formula II:

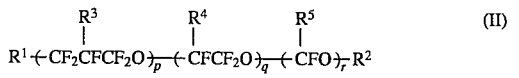

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above; provided that the molecular weight of the compound of formula (II) is from 500 to 100,00 and that all of p, q and r do not represent 0 at the same time.

2. A cosmetic of claim 1, wherein said liquid perfluoro organic compound is a perfluoro polyether represented by the following formula (II):

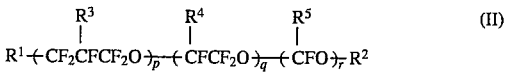

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon and p, q and r represent each a number of 0 or above value; provided that the molecular weight of the compound of the formula (II) is from 500 to 100,000 and that all of p, q and r do not represent 0 at the same time.

3. A cosmetic of claim 1, wherein said fluorine compound-treated powder is a powder treated with a polyfluoroalkylphosphate represented by the following formula (I):

$$[C_sF_{2s+1}C_tH_{2t}O]_lPO(OM)_{3-l} \quad (I)$$

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8.

4. A cosmetic comprising the following components (A), (B) and (C):

(A) a fluorine compound-treated powder,
wherein said fluorine compound is selected from the group consisting of polyfluoroalkylphosphate represented by the following formula (I):

$$[C_sF_{2s+1}C_tH_{2t}O]_lPO(OM)_{3-l} \quad (I)$$

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8; perfluoroalcohol; perfluoroepoxy compound; sulfoamide fluorophosphoric acid or a salt thereof; perfluoro-sulfuric acid or a salt thereof; perfluorocarboxylic acid or a salt thereof; and perfluoroalkylsilane, and said powder is selected from the group consisting of titanium oxide, iron oxide, ultramarine blue, zinc white, magnesium oxide, zirconium oxide, mica, sericite, talc, silica, kaolin, chromium hydroxide, carbon black, nylon powder, polymethyl methacrylate powder, styrene/divinylbenzene copolymer powder, polyethylene powder, UV-absorbing ultrafine titanium dioxide powder, UV-absorbing ultrafine zinc oxide powder and UV-absorbing fine zinc oxide flakes; and (B) a liquid perfluoro organic compound selected from the group consisting of perfluorodecalin, perfluorobutyltetrahydrofuran, perfluorooctane, perfluorononane, perfluoropentane, perfluorodecane, perfluorododecane and perfluoro polyether represented by formula II:

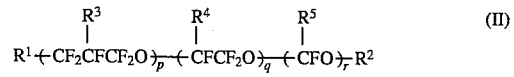

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above; provided that the molecular weight of the compound of formula (II) is from 500 to 100,00 and that all of p, q and r do not represent 0 at the same time; and (C) a silicone oil.

5. A cosmetic of claim 4, wherein said liquid perfluoro organic compound is a perfluoro polyether represented by the following formula (II):

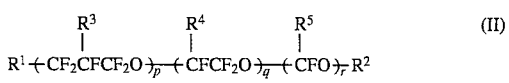

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above value; provided that the molecular weight of the compound of the formula (II) is from 500 to 100,000 and that all of p, q and r do not represent 0 at the same time.

6. A cosmetic of claim 4, wherein said fluorine compound-treated powder is a powder treated with a polyfluoroalkylphosphate represented by the following formula (I):

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8.

7. A cosmetic of claim 4, wherein said fluorine compound-treated powder amounts from 0.01 to 95% by weight, said liquid perfluoro organic compound amounts from 1 to 70% by weight and said silicone oil amounts from 1 to 70% by weight.

8. An emulsified cosmetic comprising the following components:

(A) a fluorine compound-treated powder,
wherein said fluorine compound is selected from the group consisting of polyfluoroalkylphosphate represented by the following formula (I):

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8; perfluoroalcohol; perfluoroepoxy compound; sulfoamide fluorophosphoric acid or a salt thereof; perfluorosulfuric acid or a salt thereof; perfluorocarboxylic acid or a salt thereof; and perfluoroalkylsilane, and said powder is selected from the group consisting of titanium oxide, iron oxide, ultramarine blue, zinc white, magnesium oxide, zirconium oxide, mica, sericite, talc, silica, kaolin, chromium hydroxide, carbon black, nylon powder, polymethyl methacrylate powder, styrene/divinylbenzene copolymer powder, polyethylene powder, UV-absorbing ultrafine titanium dioxide powders, UV-absorbing ultrafine zinc oxide powders and UV-absorbing fine zinc oxide flakes;

(B) a liquid perfluoro organic compound selected from the group consisting of perfluorodecalin, perfluorobutyltetrahydrofuran, perfluorooctane, perfluorononane, perfluoropentane, perfluorodecane, perfluorododecane and perfluoro polyether represented by formula II:

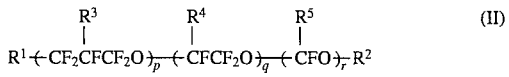

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above; provided that the molecular weight of compound of formula (II) is from 500 to 100,00 and that all of p, q and r do not represent 0 at the same time; and (D) an aqueous medium; and (E) a surfactant.

9. An emulsified cosmetic of claim 8, wherein said liquid perfluoro organic compound is a perfluoro polyether represented by the following formula (II):

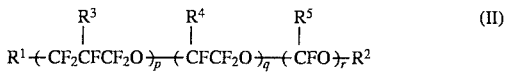

wherein $R^1$, $R^3$, $R^4$ and $R^5$ may be either the same or different and each represents a fluorine atom, a perfluoroalkyl group containing 1 to 5 carbon atoms or a perfluoroalkyloxy group containing 1 to 5 carbon atoms; $R^2$ represents a fluorine atom or a perfluoroalkyl group containing 1 to 5 carbon atoms; and p, q and r represent each a number of 0 or above value; provided that the molecular weight of the compound of the formula (II) is from 500 to 100,000 and that all of p, g and r do not represent 0 at the same time.

10. An emulsified cosmetic of claim 8, wherein said hydrophobic powder is a powder treated with a polyfluoroalkylphosphate represented by the following formula (I):

wherein s represents an integer of from 4 to 14; t represents an integer of from 1 to 16; l represents a number of from 1 to 2.5 on the average; and M, which may be the same or different from each other when l represents a number less than 2, each independently represents a hydrogen atom, an alkali metal, an ammonium group or a substituted ammonium group; provided that the total of s and t is at least 8.

11. An emulsified cosmetic of claim 8, wherein said aqueous medium is water or a mixture of water and a water-soluble alcohol.

12. An emulsified cosmetic of claim 8, wherein said fluorine compound-treated powder amounts from 0.01 to 50% by weight, said liquid perfluoro organic compound amounts from 40 to 98% by weight, said aqueous medium amounts from 0.5 to 40% by weight and said surfactant amounts from 0.01 to 20% by weight.

* * * * *